United States Patent [19]

Craig

[11] Patent Number: 4,683,293

[45] Date of Patent: Jul. 28, 1987

[54] PURIFICATION OF PICHIA PRODUCED LIPOPHILIC PROTEINS

[75] Inventor: William S. Craig, San Diego, Calif.

[73] Assignee: Phillips Petroleum Company, Bartlesville, Okla.

[21] Appl. No.: 920,385

[22] Filed: Oct. 20, 1986

[51] Int. Cl.$^4$ .......................... C07K 3/02; C07K 15/04
[52] U.S. Cl. .................................. 530/359; 435/190; 435/191; 435/197; 435/938; 514/2; 514/8; 530/371
[58] Field of Search ............... 514/2, 8; 530/371, 359; 435/190, 191, 197, 938

[56] References Cited

U.S. PATENT DOCUMENTS

| | | | |
|---|---|---|---|
| 4,427,580 | 1/1984 | Kinsella et al. | 530/371 X |
| 4,512,922 | 4/1985 | Jones et al. | 530/351 X |
| 4,540,668 | 9/1985 | Hopkins | 435/190 |
| 4,559,307 | 12/1985 | Hopkins | 435/938 X |
| 4,569,790 | 2/1986 | Koths et al. | 530/351 |
| 4,572,798 | 2/1986 | Koths et al. | 530/351 |
| 4,604,377 | 8/1986 | Fernandes et al. | 514/2 X |

FOREIGN PATENT DOCUMENTS 135435 8/1984 European Pat. Off. .

OTHER PUBLICATIONS

"Lysis of Halophilic Vibrio Alginolyticus and Vibrio Costicolus Induced by Chaotropic Anions", T. Unemoto et al, Biochimica et Biophysica Acta, 500, pp. 42–431 (1977).

"Multiple Chemical Forms of Hepatitis B Surface Antigen Produced in Yeast", D. E. Wampler et al, Proc. Natl. Acad. Sci. USA, vol. 82, pp. 6830–6834, Oct. 1985.

*Primary Examiner*—Howard E. Schain
*Attorney, Agent, or Firm*—S. E. Reiter

[57] ABSTRACT

Method for the selective extraction of desired lipophilic proteins from transformed cells of the genus *Pichia* by cell lysis in the presence of chaotrophic salts is disclosed. The total protein extracted under the invention cell lysis conditions is reduced while the recovery of desired lipophilic proteins remains relatively constant, thereby producing a cell extract with enhanced concentration of the desired lipophilic protein relative to a control cell extract.

9 Claims, No Drawings

4,683,293

PURIFICATION OF PICHIA PRODUCED LIPOPHILIC PROTEINS

This invention relates to protein recovery and purification. In one aspect, this invention relates to the separation of soluble protein from cell debris. In another aspect, this invention relates to the selective extraction of proteins.

BACKGROUND

Recombinant DNA technology is rapidly becoming a powerful tool for the production of peptides and proteins of interest for a variety of diagnostic, therapeutic and chemical applications, and the like. One problem frequently encountered, however, is the need to obtain the desired protein in a purified form free of contaminating proteins which are also produced during expression of the desired product. The present invention is directed to improved methods for recovery of proteins produced by recombinant DNA techniques.

OBJECTS OF THE INVENTION

An object of the present invention, therefore, is to provide a method for the efficient recovery of desired proteins produced by genetically modified yeast organisms.

This and other objects of the present invention will become apparent from inspection of the disclosure and claims herein provided.

STATEMENT OF THE INVENTION

In accordance with the present invention, it has been discovered that lipophilic proteins produced by genetically modified strains of Pichia can be selectively recovered by use of a lysis buffer containing chaotropic salts. The disruption of strains of Pichia in the presence of such lysis buffers reduces the total amount of protein extracted while exerting little effect on the extraction of the desired lipophilic proteins. Thus, the soluble cell extract obtained in the practice of the present invention contains an enhanced level of lipophilic protein relative to all other proteins contained in the extract, thereby simplifying any further purification steps to which the desired lipophilic protein is subjected.

DETAILED DESCRIPTION OF THE INVENTION

In accordance with the present invention, lipophilic proteins produced by host cells of the genus *Pichia* are extracted by a method comprising:

(a) subjecting the cells to cell breaking conditions for a time sufficient to cause breakage of substantially all of the cells, wherein said breakage is carried out in the presence of an extraction medium comprising
   in the range of about 1 up to 8 molar concentration of at least one chaotropic salt,
   in a medium buffered at a pH suitable to maintain the desired protein in a stable form, typically in the range of about 6 up to 8, and (b) recovering the soluble fraction obtained from step (a).

The soluble fraction recovered in accordance with the present invention can then be further treated employing techniques known by those of skill in the art to further concentrate and purify the desired protein. Thus, the protein in the soluble fraction can be concentrated by dialysis, passage through a reverse phase resin followed by elution with a minimum volume of solvent, precipitation, ultrafiltration, lyophilization, and the like. Techniques available for further purification of the desired protein include size fractionation employing size exclusion resins, high performance liquid chromatography, ion exchange, hydrophobic chromatography, and the like.

As employed in this disclosure, the term "lipophilic protein" refers to those proteins that have a tendency to associate with lipid membranes, or, in the presence of lipid or lipid-like material, assemble into micellar-like structures. Such proteins typically have a high content of hydrophobic amino acids, i.e., isoleucine, valine, leucine, phenylalanine, tryptophan, and alanine.

Exemplary lipophilic proteins include, but are not limited to:

all forms of the hepatitis B surface antigen, including the S-form, the $preS_1$-form, the $preS_2$-form, and the like;
phosphatidylserine decarboxylase (from *E. coli*);
lambda bacteriophage D-protein;
low density lipoprotein (LDL);
high density lipoprotein (HDL); and
dihydroorotate dehydrogenase.

As employed in this disclosure, the term "chaotropic salt" refers to salts whose anions favor the transfer of apolar groups to water. Such salts include compounds which contain the thiocyanate ion, halide ions such as iodide and bromide, and hypohalite ions such as perchlorate, as well as cations such as, for example, lithium, calcium and barium.

Exemplary chaotropic salts useful in the practice of the present invention include sodium thiocyanate, potassium thiocyanate, sodium iodide, potassium iodide, sodium hypochlorite, lithium chloride, lithium bromide, guanidinium hydrochloride, guanidinium thiocyanate, urea, and the like.

The production of lipophilic proteins by *Pichia* can be accomplished by genetic modification of suitable host strains of Pichia with DNA sequences which code for the desired protein. The appropriate DNA sequences which code for a desired lipophilic protein are readily available to those of skill in the art by, for example, isolation from natural sources, by construction of a synthetic DNA sequence, and the like. Specific techniques for the manipulation of DNA in strains of Pichia are disclosed in articles appearing in volume 5 of Molecular and Cellular Biology at pages 1111 and 3376 (1985).

The invention extraction process is carried out by subjecting the cells to cell breaking conditions for a time sufficient to cause breakage of substantially all of the cells. This cell breakage is carried out in the presence of an extraction medium comprising in the range of about 1 up to 8 molar concentration of at least one chaotropic salt in a medium buffered at a pH suitable to maintain the desired protein in a stable form, typically in the range of about 6 up to 8. Optionally, to minimize protein degradation during the extraction procedure, anti-protease agents, such as phenylmethylsulfonyl fluoride may be included in the lysis buffer.

Typically employed for cell breakage in the practice of the present invention is homogenization in a bead mill or similar apparatus. The time required for cell breaking is a function of the susceptibility of the cell walls to breakage, the severity of the homogenization conditions, the presence and concentration of added components in the lysis buffer, and the like. Typically, cells are subjected to breaking conditions for a time in the range of about 0.5 up to 30 minutes; preferably times in the range of about 1 up to 5 minutes being employed.

The temperature employed during cell breakage is generally controlled so as to minimize the action of proteindegrading enzymes. Thus, cell breaking is generally carried out at a temperature in the range of about 0° up to 10° C., preferably about 0° C., in order to minimize the amount of degradation of the desired protein during the breakage step, thereby enhancing the yield of desired protein recovered from the cells being broken.

Once cells have been broken, the soluble fraction is recovered by removing cell debris by techniques known to those of skill in the art, e.g., centrifugation or tangential filtration. The resulting cell free broth is enriched in the desired lipophilic protein relative to broth obtained by merely breaking cells and recovering the soluble fraction therefrom.

If desired, the thus treated broth can be further treated to recover a concentrated fraction of the desired lipophilic protein by various techniques known to those of skill in the art, such as for example, acid precipitation, filtration, chromatography, solvent evaporation and the like.

The present invention will now be described in greater detail by reference to the following nonlimiting examples.

EXAMPLE I

The extraction of hepatitis B surface antigen (HBsAg) 22 nm particles from Pichia cells transformed with vector pBSAGI5I (available in an *E. coli* host from the Northern Regional Research Center of the US Department of Agriculture, Peoria, ILL., with the accession number (NNRL B-18021) is described below.

Cultures of *P. pastoris* were grown to a cell density in the range of 10 up to 100 optical density units (600 nm) per milliliter. An aliquot of 100 optical density units was removed to a 13×100 mm borosilicate culture tube and washed twice with 20 volumes of lysing buffer (recipe follows).

To the pelleted cells (IEC clinical centrifuge) was added 0.5 g of acid-washed glass beads (0.5 mm) followed by 0.35 mL of lysing buffer. The lysing buffer contained either 0.5 M NaCl and 0.1% Triton X-100 (wt/vol.) as a control, or a 2 M or 3 M concentration of a chaotropic salt in the presence or absence of 0.1% Triton X-100. All solutions were buffered at pH 7.5 with 10 mM sodium phosphate. The mixture was agitated for eight, one-minute intervals at maximum speed using a vortex mixer. Between intervals the mixture was cooled on ice for not less than one minute. The tubes were preferably held at a 20°–40° angle while vortexing to achieve maximum breakage. After lysing was completed the solution of broken cells was removed, the glass beads were washed with 0.35 mL of lysing buffer, and the two solutions were combined and submitted to centrifugation for 15 minutes at 13,000×g. The supernates were removed and assayed for immunoreactive HBsAg particle (Ausria assay) and total protein (Bradford). Results as presented in Table I (a).

EXAMPLE II

To further illustrate the method of the invention, an 80 mL slurry (one part packed cells/two parts lysing buffer, v/v) was subjected to the action of a cell disrupter (Impandex, Inc.) using a 64 mm agitator disc at 4500 r.p.m. The lysing buffer contained either 0.5 M NaCl and 0.1% Triton (w/v) or 3 M KSCN. The supernates were assayed for HBsAg (Ausria) and total protein (Bradford). Results are presented in Table I (b).

TABLE I

| Lysing Conditions | I HBsAg particle ($\mu$g/mL) | II Total Protein (mg/mL) | III HBsAg/Protein (wt. %) |
|---|---|---|---|
| (a) Salt (conc.) | | | |
| NaCl (0.5 M) + Triton | 230 | 10.1 | 2.3 |
| KI (2 M) + Triton | 14 | 1.4 | 1.0 |
| KI (2 M) − Triton | 169 | 2.4 | 7.0 |
| KSCN (3 M) + Triton | <10 | 1.9 | <0.5 |
| KSCN (3 M) − Triton | 222 | 3.5 | 6.3 |
| (b) Cell Disrupter | | | |
| NaCl (0.5 M) + Triton | 600 | 32.5 | 1.8 |
| KSCN (3 M) | 803 | 10.6 | 7.6 |

While none of the conditions containing a chaotropic salt (KI or KSCN) yields HBsAg particle values significantly higher than the control (Column I), it is clear that the chaotropic salts inhibit the release of total protein (Column II), thereby increasing the specific activity of HBsAg particle 2 to 5-fold (Column III).

The examples have been provided merely to illustrate the practice of the invention and should not be read as to limit the scope of the invention or the appended claims in any way. Reasonable variations and modifications, not departing from the essence and spirit of the invention, are contemplated to be within the scope of patent protection desired and sought.

That which is claimed is:

1. A method for the extraction of lipophilic proteins from host cells of the genus Pichia which comprises
   (a) subjecting the cells to cell breaking conditions for a time sufficient to cause breakage of substantially all of the cells, wherein said breakage is carried out in the presence of an extraction medium comprising
      in the range of about 1 up to 8 molar concentration of at least one chaotropic salt, in a medium buffered at a pH suitable to maintain said lipophilic protein in a stable form, and
   (b) recovering the soluble fraction obtained from step (a).

2. A method in accordance with claim 1 wherein said pH is maintained in the range of about 6 up to 8.

3. A method in accordance with claim 1 wherein said lipophilic protein is a protein which has a tendency to associate with lipid membranes.

4. A method in accordance with claim 1 wherein said lipophilic protein is a protein which assembles into micellar-like structures in the presence of lipid or lipid-like material.

5. A method in accordance with claim 1 wherein said lipophilic protein is selected from the group consisting of:
   the S-form of the hepatitis B surface antigen,
   the preS$_1$-form of the hepatitis B surface antigen,
   the preS$_2$-form of the hepatitis B surface antigen,
   phosphatidylserine decarboxylase (from *E. coli*),
   lambda bacteriophage D-protein,
   low density lipoprotein (LDL),
   high density lipoprotein (HDL), and
   dihydroorotate dehydrogenase.

6. A method in accordance with claim 1 wherein said cell breaking is carried out at a temperature in the range of 0 up to 10° C. for a time in the range of about 0.5 up to 30 minutes.

7. A method in accordance with claim 1 wherein said chaotropic salt is selected from the group consisting of:
sodium thiocyanate
potassium thiocyanate,
sodium iodide,
potassium iodide,
sodium hypochlorite,
lithium chloride,
lithium bromide,
guanidinium hydrochloride,
guanidinium thiocyanate,
urea,
and mixtures of any two or more thereof.

8. A method in accordance with claim 1 wherein the step (b) recovery of said soluble fraction is accomplished by centrifugation of the solution containing disrupted cells.

9. A method in accordance with claim 1 further comprising:
    (c) treating the soluble fraction obtained from step (b) to recover a concentrated fraction of the lipophilic protein therefrom.

* * * * *